United States Patent [19]

Hwang

[11] Patent Number: 4,832,061
[45] Date of Patent: May 23, 1989

[54] DOUBLE-THREADED TOOTH PICK

[76] Inventor: Ying-Teh Hwang, 10-4 f, 62, Chang Chun Rd., Taipei, Taiwan

[21] Appl. No.: 485,742

[22] Filed: Apr. 18, 1983

[51] Int. Cl.⁴ ............................................... A61C 15/00
[52] U.S. Cl. ................................... 132/329; 433/141; 433/216
[58] Field of Search ............... 433/141, 143, 142, 102, 433/165, 216; 132/89, 93

[56] References Cited

U.S. PATENT DOCUMENTS

| | | | |
|---|---|---|---|
| 1,170,523 | 2/1916 | Fernald | 433/141 |
| 1,369,582 | 2/1921 | Wagner | 433/142 |
| 1,500,798 | 7/1924 | Campodonico | 433/141 |
| 4,280,808 | 7/1981 | Johnsen | 433/141 |
| 4,326,547 | 4/1982 | Verplank | 132/93 X |

FOREIGN PATENT DOCUMENTS 2016931 9/1979 United Kingdom ................. 132/93

Primary Examiner—Richard J. Apley
Assistant Examiner—Robert W. Bahr
Attorney, Agent, or Firm—Bacon & Thomas

[57] ABSTRACT

A double-threaded tooth pick bar formed with a double-threaded portion on one end of the pick bar and a slim portion terminating in a hook at the other end for easier and safer removal of plaque and food debris lodged between the teeth.

1 Claim, 1 Drawing Sheet

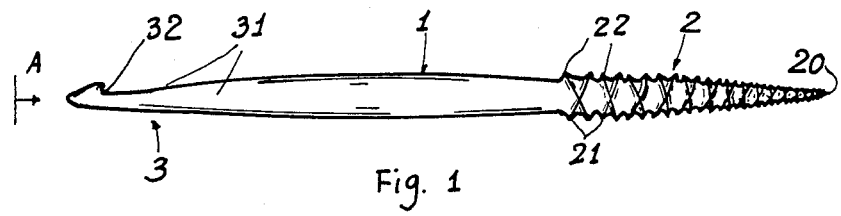
Fig. 1
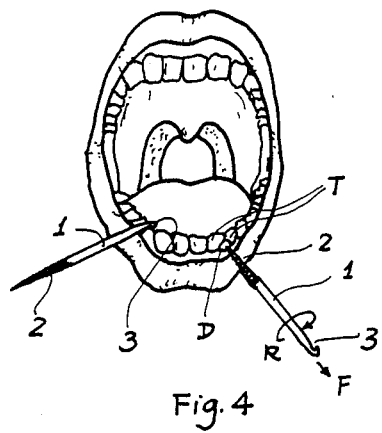
Fig. 3
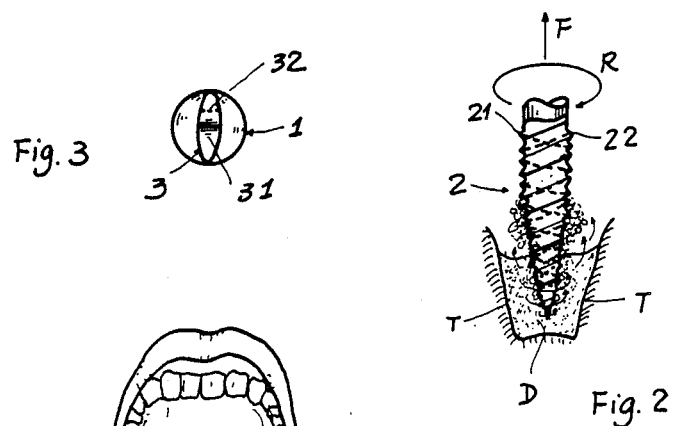
Fig. 2
Fig. 4

DOUBLE-THREADED TOOTH PICK

BACKGROUND OF THE INVENTION

Conventional tooth picks are used to remove plaque and food debris lodged between the teeth. However, the conventional tooth pick is formed with straight tapered needle end which make it very difficult to remove plaque and food debris lodged in the rear corner behind the teeth. Whenever picking out the plaque and food debris lodged in the aperture of the teeth, the straight tapered end of a conventional tooth pick is always reciprocatively operated to remove these lodged materials. This could easily injure the gums or damage the tooth enamel. Such a straight needle end, when poked into lodged materials and withdrawn outwards, lacks pulling strength and is thus not able to pull the plaque and food debris efficiently.

SUMMARY OF THE INVENTION

The object of the present invention is to provide a tooth pick having a double-threaded portion which may be poked into lodged materials, rotated, and then pulled outwards such that plaque and food debris lodged between teeth can be easily withdrawn without injury or damage to the teeth and gums.

Another object of the present invention is to provide a tooth pick having a slim portion which is tapered, flattened and terminates with a hook for easy removal of plaque and food debris lodged behind the teeth.

BRIEF DESCRIPTION OF THE DRAWINGS

FIG. 1 is a perspective drawing of the present invention.

FIG. 2 is a partial sectional drawing of the double-threaded portion of the present invention.

FIG. 3 is a side-view drawing taken from direction A of FIG. 1.

FIG. 4 is an illustration to show the present invention in use.

DETAILED DESCRIPTION

As shown in the figures, the present invention comprises a pick bar 1, a double-threaded portion 2 formed on one end of bar 1 and a slim portion 3 formed on another end of bar 1.

The double-threaded portion 2 is tapered from the central pick bar and terminates with tapered end 20. In portion 2, there are two threads, one of which is a right thread 21 wound rightwards and the other is a left thread 22 wound leftwards. Both threads 21, 22 are crossed with each other.

Slim portion 3 comprises a tapered flat portion 31 which terminates with a hook 32.

When using the present invention as shown in FIGS. 4 and 2, the double-threaded portion 2 is poked into the plaque or food debris D lodged between the teeth T and rotated in direction R and then pulled outwards (direction F). The lodged materials will be easily wound onto the double-threaded portion 2. The operation for removing plaque and food debris comprises two steps. They include one step of rotating the bar (R) and the second step of withdrawing the bar (F). The bar rotation of the present invention is quite different from the reciprocative movement of conventional tooth pick, which could easily injure the gums and damage the teeth enamel. The present invention is quicker and more efficient in removing lodged materials and less harmful to the teeth than a conventional tooth pick.

The slim portion of the present invention having hook 32 may be extended into the rear surface of teeth for removing the plaque and food debris lodged behind the teeth more efficiently than conventional tooth pick with straight tapered end. The slim and flat end can also be easily poked into the aperture between the teeth for a smoother and safer operation without injury to the teeth and gums.

I claim:

1. A tooth pick comprising an elongated bar including a first end being tapered to a point and threaded in a double helix and with the threads being wound in opposite directions about the bar, and a second end being tapered to a flat section and terminating with a hook.

* * * * *